United States Patent
Chornenky et al.

[11] Patent Number: 6,095,966
[45] Date of Patent: Aug. 1, 2000

[54] X-RAY DEVICE HAVING A DILATION STRUCTURE FOR DELIVERING LOCALIZED RADIATION TO AN INTERIOR OF A BODY

[75] Inventors: Victor I. Chornenky, Minnetonka; Michael R. Forman, Vadnais Heights, both of Minn.; Robert A. Ganz, 2545 Chicago Ave., Minneapolis, Minn. 55404

[73] Assignees: XRT Corp., St. Paul; Robert A. Ganz, Minneapolis, both of Minn.

[21] Appl. No.: 09/027,010

[22] Filed: Feb. 20, 1998

Related U.S. Application Data

[60] Provisional application No. 60/044,424, Feb. 21, 1997.

[51] Int. Cl.[7] .................................................... H01J 35/32
[52] U.S. Cl. .............................................................. 600/3
[58] Field of Search ................................. 600/1–8, 407, 600/436; 378/65, 70, 145; 604/20–22, 113, 114; 606/1, 2, 7, 32

[56] References Cited

U.S. PATENT DOCUMENTS

| Re. 34,421 | 10/1993 | Parker et al. . |
|---|---|---|
| 1,786,373 | 12/1930 | Walker . |
| 1,881,448 | 10/1932 | Forde et al. . |
| 2,173,258 | 9/1939 | Lederer . |
| 2,467,812 | 4/1949 | Clapp . |
| 2,766,385 | 10/1956 | Herrnring et al. . |
| 3,005,096 | 10/1961 | Chynoweth . |
| 3,073,960 | 1/1963 | Guentner et al. . |
| 3,125,679 | 3/1964 | Ohde et al. . |

(List continued on next page.)

FOREIGN PATENT DOCUMENTS

| 0 359 724 A2 | 3/1990 | European Pat. Off. . |
|---|---|---|
| 0 359 724 A3 | 3/1990 | European Pat. Off. . |
| 0 572 170 A1 | 12/1993 | European Pat. Off. . |
| 0 718 864 A1 | 6/1996 | European Pat. Off. . |
| 0 860 180 A2 | 8/1998 | European Pat. Off. . |
| 0 860 181 A2 | 8/1998 | European Pat. Off. . |
| 2 672 734 | 8/1992 | France . |
| 2054738 | 5/1972 | Germany . |
| 26 08 418 | 9/1977 | Germany . |
| 58-145098 | 8/1983 | Japan . |
| 8-153460 | 6/1996 | Japan . |
| 814331 | 3/1981 | Russian Federation . |
| 230183 | 3/1925 | United Kingdom . |
| 997352 | 7/1965 | United Kingdom . |
| WO 95/20241 | 7/1995 | WIPO . |
| WO 96/02059 | 1/1996 | WIPO . |
| WO 97/06549 | 2/1997 | WIPO . |
| 97/07740 | 3/1997 | WIPO .................................. 600/407 |
| WO 97/07740 | 3/1997 | WIPO . |

OTHER PUBLICATIONS

Chornenky, V., "The Soft X–Ray System" (Ch. 14), *Handbook of Vascular Brachytherapy*, Waksman et al., Eds., Martin Dunitz Ltd., London, Mar. 1998 (6 pages).

PCT International Search Report (English Translation Abstract of PCT/US96/13629 included) (4 pages) Jun. 1997.

Brochure: "Dunlee DL–1 Stationary Anode Insert"Dunlee Corporation, Bellwood, IL 60104, Jun. 1972.

Asano, et al., *Jp. J. Appl. Phys.*, 31(Part1, 9B):3098–3101 (Sep. 1992).

Brady, et al., *Gynecologic Oncology*, 2:314–323 (1974).

Condado, et al., 1 page, *Discoveries in Radiation for Restenosis*, Emory University School of Medicine (Jan. 1996).

(List continued on next page.)

*Primary Examiner*—Samuel I Gilbert
*Attorney, Agent, or Firm*—Merchant & Gould P.C.

[57] ABSTRACT

Generally, the present invention provides a device for insertion into a body of a subject being treated to deliver localized x-ray radiation, and a method for use of such a device. The device includes an anode and a cathode, disposed within a vacuum housing. The device further includes a balloon coupled to and circumferentially surrounding the vacuum housing, and a fluid loop for circulating a cooling fluid proximate to the vacuum housing. A method for delivering localized x-ray radiation to an interior passage of a body is also described, including the steps of positioning an x-ray device at the passage to be treated and applying a high voltage to the x-ray producing unit to produce localized x-ray radiation.

15 Claims, 3 Drawing Sheets

U.S. PATENT DOCUMENTS

| | | |
|---|---|---|
| 3,256,439 | 6/1966 | Dyke et al. . |
| 3,348,051 | 10/1967 | Weighart et al. . |
| 3,381,129 | 4/1968 | Dufschmid . |
| 3,388,314 | 6/1968 | Gould . |
| 3,484,721 | 12/1969 | Bond et al. . |
| 3,508,059 | 4/1970 | Vanderpool . |
| 3,538,919 | 11/1970 | Meyer . |
| 3,564,251 | 2/1971 | Youmans . |
| 3,582,702 | 6/1971 | Almer . |
| 3,617,939 | 11/1971 | Bond et al. . |
| 3,628,021 | 12/1971 | MacDonald . |
| 3,691,417 | 9/1972 | Gralenski . |
| 3,714,486 | 1/1973 | McCrary . |
| 3,752,990 | 8/1973 | Fischer . |
| 3,866,050 | 2/1975 | Whitfield . |
| 3,878,394 | 4/1975 | Golden . |
| 3,883,760 | 5/1975 | Cunningham, Jr. . |
| 3,920,999 | 11/1975 | Drexler et al. . |
| 3,970,884 | 7/1976 | Golden . |
| 3,987,281 | 10/1976 | Hodes . |
| 4,058,486 | 11/1977 | Mallozzi et al. . |
| 4,060,731 | 11/1977 | Rissi . |
| 4,097,759 | 6/1978 | Furbee et al. . |
| 4,104,526 | 8/1978 | Albert . |
| 4,104,530 | 8/1978 | Weis . |
| 4,104,531 | 8/1978 | Weiss . |
| 4,104,532 | 8/1978 | Weiss . |
| 4,109,154 | 8/1978 | Taumann . |
| 4,117,334 | 9/1978 | Strausts . |
| 4,143,275 | 3/1979 | Mallozzi . |
| 4,158,138 | 6/1979 | Hellstrom . |
| 4,163,901 | 8/1979 | Azam et al. . |
| 4,164,680 | 8/1979 | Villalobos . |
| 4,191,193 | 3/1980 | Seo . |
| 4,344,181 | 8/1982 | Baecklund . |
| 4,359,660 | 11/1982 | Smith et al. . |
| 4,368,538 | 1/1983 | McCorkle . |
| 4,563,769 | 1/1986 | Madsen . |
| 4,607,380 | 8/1986 | Oliver . |
| 4,636,195 | 1/1987 | Wolinsky . |
| 4,646,338 | 2/1987 | Skillicorn . |
| 4,669,467 | 6/1987 | Willett et al. . |
| 4,670,894 | 6/1987 | Birnbach et al. . |
| 4,694,480 | 9/1987 | Skillcorn . |
| 4,701,941 | 10/1987 | Szirmai et al. . |
| 4,702,228 | 10/1987 | Russell, Jr. et al. . |
| 4,715,054 | 12/1987 | Kato et al. . |
| 4,763,671 | 8/1988 | Goffinet . |
| 4,789,997 | 12/1988 | Madsen et al. . |
| 4,794,931 | 1/1989 | Yock . |
| 4,800,581 | 1/1989 | Kujirai et al. . |
| 4,824,436 | 4/1989 | Wolinsky . |
| 4,856,036 | 8/1989 | Malcolm . |
| 4,913,142 | 4/1990 | Kittrell et al. . |
| 4,924,485 | 5/1990 | Hoeberling . |
| 4,966,596 | 10/1990 | Kuntz et al. . |
| 4,976,266 | 12/1990 | Huffman et al. . |
| 4,979,199 | 12/1990 | Cueman et al. . |
| 5,042,486 | 8/1991 | Pfeiler et al. . |
| 5,059,166 | 10/1991 | Fischell et al. . |
| 5,077,771 | 12/1991 | Skillcorn et al. . |
| 5,087,244 | 2/1992 | Wolinsky et al. . |
| 5,090,043 | 2/1992 | Parker et al. . |
| 5,099,845 | 3/1992 | Besz et al. . |
| 5,101,422 | 3/1992 | Thiel et al. . |
| 5,106,360 | 4/1992 | Ishiwara et al. . |
| 5,148,463 | 9/1992 | Woodruff et al. . |
| 5,153,900 | 10/1992 | Nomikos et al. . |
| 5,165,093 | 11/1992 | Miller et al. . |
| 5,199,939 | 4/1993 | Dake et al. . |
| 5,222,116 | 6/1993 | Eloff et al. . |
| 5,228,176 | 7/1993 | Bui et al. . |
| 5,264,801 | 11/1993 | Decou, Jr. et al. . |
| 5,290,275 | 3/1994 | Kittrell et al. . |
| 5,313,949 | 5/1994 | Yock . |
| 5,313,950 | 5/1994 | Ishikawa et al. . |
| 5,364,336 | 11/1994 | Carr . |
| 5,369,679 | 11/1994 | Sliski et al. . |
| 5,402,790 | 4/1995 | Jang et al. . |
| 5,414,748 | 5/1995 | Upadhya . |
| 5,422,926 | 6/1995 | Smith et al. ............................ 378/121 |
| 5,425,735 | 6/1995 | Rosen et al. . |
| 5,428,658 | 6/1995 | Oettinger et al. . |
| 5,437,277 | 8/1995 | Dumoulin et al. . |
| 5,442,678 | 8/1995 | Dinsmore et al. . |
| 5,444,254 | 8/1995 | Thomson . |
| 5,452,720 | 9/1995 | Smith et al. . |
| 5,453,575 | 9/1995 | O'Donnell et al. . |
| 5,454,809 | 10/1995 | Janssen . |
| 5,465,732 | 11/1995 | Abele . |
| 5,469,490 | 11/1995 | Golden et al. . |
| 5,474,075 | 12/1995 | Goldberg et al. . |
| 5,503,613 | 4/1996 | Weinberger . |
| 5,504,799 | 4/1996 | Suzuki . |
| 5,511,107 | 4/1996 | Sliski . |
| 5,528,652 | 6/1996 | Smith et al. . |
| 5,549,553 | 8/1996 | Ressemann et al. . |
| 5,566,221 | 10/1996 | Smith et al. ............................ 378/145 |
| 5,621,780 | 4/1997 | Smith et al. ............................ 378/65 |
| 5,623,139 | 4/1997 | Sliski . |
| 5,635,709 | 6/1997 | Sliski et al. . |
| 5,643,171 | 7/1997 | Bradshaw et al. . |
| 5,741,246 | 4/1998 | Prescott . |
| 5,748,689 | 5/1998 | Smith . |
| 5,748,699 | 5/1998 | Smith ...................................... 378/65 |

OTHER PUBLICATIONS

Fischell, et al., *Circulation*, 90(6): 2956–2963 (Dec. 1994).

Geissler, et al., *Physics Letters A*, 176:387–392 (1993).

Gundel, et al., *Nuclear Instruments and Methods in Physics Research*, A280:1–6 (1989).

Gundel, et al., *J. Appl. Phys.*, 69:975–982 (Jan. 1991).

Hehrlein, et al., *Circulation*, 92(6):1570–1575 (Sep. 1995).

Levine, *Scientific America Science & Medicine*, 1:(5):16–25 (Nov.–Dec. 1994).

March, et al., *Circulation*, 87(1):184–191 (Jan. 1993).

Matsuda, et al., *Journal of Materials Science*, 21:649–658 (1986).

Matsuda, et al., *Journal of Material Science*, 23:509–514 (1988).

Papillon, *Diseases of the Colon & Rectum*, 27(11) :695–700 (Nov. 1984).

Phillips, *Radiology*, 90(3):525–531 (Mar. 1968).

Sugiyama, et al., *Materials Science Forum*, 54&55:141–152 (1990).

Riege, *Nucl. Inst. and Meth. in Phys. Res.*, A340:80–89 (1994).

Schwartz, et al., *JACC*, 19(5):1106–1113 (Apr. 1992).

Soares, et al., *Nuclear Technology Publishing*, 47(174):367–372 (1993).

Strickland, *Clinical Radiology—The J. of the Faculty of Radiologists*, XVI(1–4):112–118 (Jan. to Oct. 1965).

Verin et al., *Circulation*, 92:(8):2284–2290 (Oct. 1995).

Wang, et al., *Int. J. Radiation Oncology Biol. Phys.*, 9 (8):1185–1189 (Aug. 1983).

Waksman, et al., *Circulation*, 92(6):1383–1386 (Sep. 1995).

Waksman, et al., *Circulation*, 92(10): 3025–3031 (Nov. 1995).

Waksman, et al., *Circulation*, 91(5):1533–1539 (Mar. 1995).

Wiedermann, et al., *JACC*, 23(6):1491–1498 (May 1994).

Wiedermann, et al., *JACC*, 25(6):1451–1456 (May 1995).

Wiedermann, et al., "Effects of high–dose intracoronary irradiation on vasomotor function and smooth muscle histopathology", pp.H125–H132 (1994).

FIG. 3
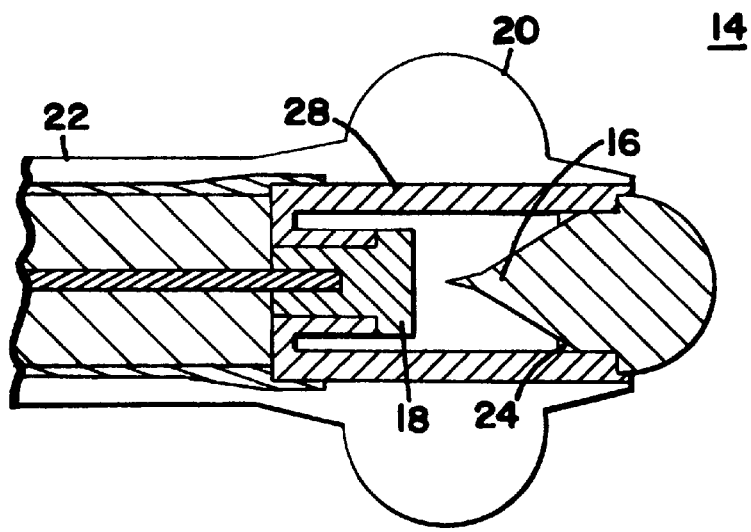
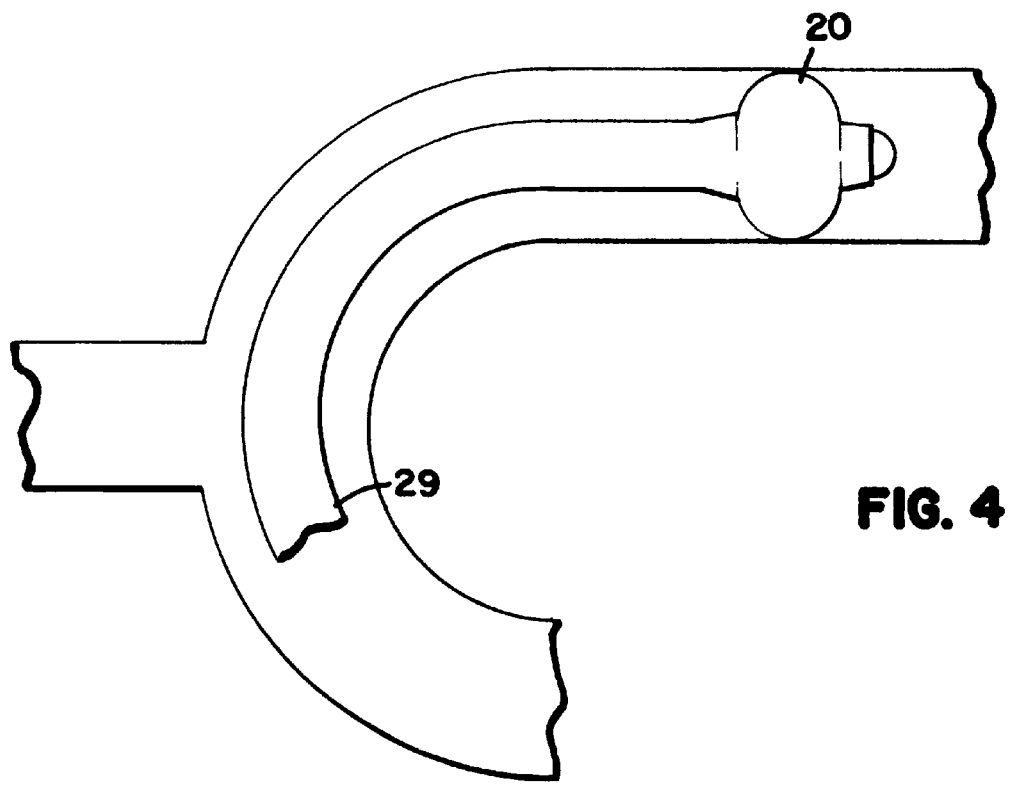
FIG. 4

X-RAY DEVICE HAVING A DILATION STRUCTURE FOR DELIVERING LOCALIZED RADIATION TO AN INTERIOR OF A BODY

This application claims benefit of professional application 60/044,424, filed Feb. 21, 1997.

I. FIELD OF THE INVENTION

The present invention is directed to x-ray devices and methods of use, and more particularly to an x-ray device and method for fabrication for delivering localized radiation to vessels, lumens, or cavities of a body, such as the esophagus, to treat Barrett's Disease, prevent restenosis after dilatation of pyloric strictures and treat other conditions.

II. BACKGROUND OF THE INVENTION

In the medical field, small and effective medical devices are needed for many applications to treat the interior of the body. Also, doctors and scientists are continually striving to find less invasive ways to treat patients. By using treatments that are less intrusive to the body, doctors can greatly reduce the stress on the patient's systems and exposure to infection. For example, small, nonintrusive medical devices are extremely beneficial when applied to treat the esophagus, which is approximately one to two centimeters in diameter.

Effective medical devices to treat the esophagus could benefit tens of millions of Americans who suffer from gastroesophageal reflux disease (GERD). GERD is characterized by a backward flow of the stomach and duodenal contents into the esophagus. These conditions result when the valve at the junction between the esophagus and the stomach does not function properly. When this occurs frequently, it is termed chronic GERD or reflux esophagitis. The symptoms of this condition are dyspepsia, or discomfort in the esophagus after meals, burning chest, upper abdominal pain, sour taste, and regurgitation.

Medical research has revealed that the acidic stomach contents cause anatomic abnormalities of the epithelium, or lining, of the esophagus during reflux. The cell type of the epithelium of the esophagus changes from a squamous, or circular-shaped cell, to a columnar, or rectangular-shaped, cell type. This cellular damage of the epithelium is termed Barrett's esophagus.

Barrett's esophagus is a precursor for cancer of the gastroesophageal system. Barrett's-associated malignancies strike approximately 10,000 people per year. There is a high rate of progression from reflux disease to Barrett's esophagus. In fact, 90 percent of patients with reflux symptoms who have an endoscopic examination show anatomic abnormalities of the epithelium.

Diagnosis of cancer in Barrett's esophagus ordinarily leads to removal of the diseased segment of the esophagus. However, an effective treatment of Barrett's disease could prevent the progression to cancer and could therefore reduce the need for this painful and drastic procedure. An effective treatment for Barrett's esophagus could improve the lives of many people. Ultrasound and argon-ion plasma treatments have been suggested to treat Barrett's esophagus, but these techniques are in early experimental stages and have not been proven effective. It is believed that photodynamic therapy is also a possibility.

Many other disorders could be treated with small, effective medical devices capable of accessing the interior of the body. For example, one disorder of the gastrointestinal system is pyloric strictures. Pyloric strictures occur in the pylorus, or distal aperture of the stomach. The pylorus is surrounded by a strong band of circular muscle, through which the stomach contents are emptied into the duodenum.

Pyloric strictures can be subjected to dilatation to open the pylorus passage. However, the pylorus frequently thickens in response to the dilatation. Repeated dilatation has been used to treat pyloric strictures, but has not proven to be an effective long-term solution. There is a need for treatments to prevent this recurrent thickening of the pylorus.

Thus, there is a need for effective methods and devices to treat many parts of the interior of the body with minimal intrusion. The development of a treatment method and device for Barrett's esophagus and pyloric strictures is especially needed and could benefit millions of people.

III. SUMMARY OF THE INVENTION

The present invention directed to an x-ray device for delivering localized radiation to the interior of a body. The device includes an anode and a cathode, disposed within a vacuum housing, the anode and the cathode arranged to produce the localized x-ray radiation, a flexible shaft having distal and proximal portions, where the vacuum housing is coupled to the distal portion of the shaft, and a balloon coupled to and circumferentially surrounding the vacuum housing, the balloon being in fluid communication with a fluid loop for circulating a fluid through an interior of the balloon, the balloon being inflatable by the fluid.

In one embodiment of the invention, the balloon is elastic. In another embodiment, the outer diameter of the vacuum housing and the shaft is less than or equal to approximately three millimeters. In another embodiment, the shaft includes a cooling fluid loop for circulating a fluid to the distal portion of the shaft. The vacuum housing is cylindrically shaped in another embodiment. In another embodiment, the x-ray device is sized to be able to deliver the localized radiation to the interior of the esophagus.

The present invention is further embodied in an x-ray device for delivering localized radiation to the interior of a body, including an anode and a cathode disposed within a vacuum chamber, and an elastic balloon circumferentially surrounding the x-ray unit, the balloon being in fluid communication with a fluid loop for providing fluid to an interior of the balloon.

A method for delivering localized x-ray radiation to an interior passage of a body is also encompassed by an embodiment of the present invention. The method includes the steps of positioning the above-described x-ray device at the passage to be treated, and applying a high voltage to the x-ray producing unit. The method may further comprise providing fluid to the interior of the dilating balloon. The x-ray device may be cooled using, for example, the fluid in the dilating balloon or by circulating a cooling fluid to the x-ray device. An alternative embodiment includes the step of disposing the x-ray device inside an endoscope.

IV. BRIEF DESCRIPTION OF THE DRAWINGS

The invention may be more completely understood in consideration of the detailed description of various embodiments of the invention which follows in connection with the accompanying drawings, in which:

FIG. 3 shows an exploded cross-sectional view of x-ray source components of the present invention; and FIG. 4 shows a view of an x-ray device as it traverses an interior passage of a patient.

Figure 1:
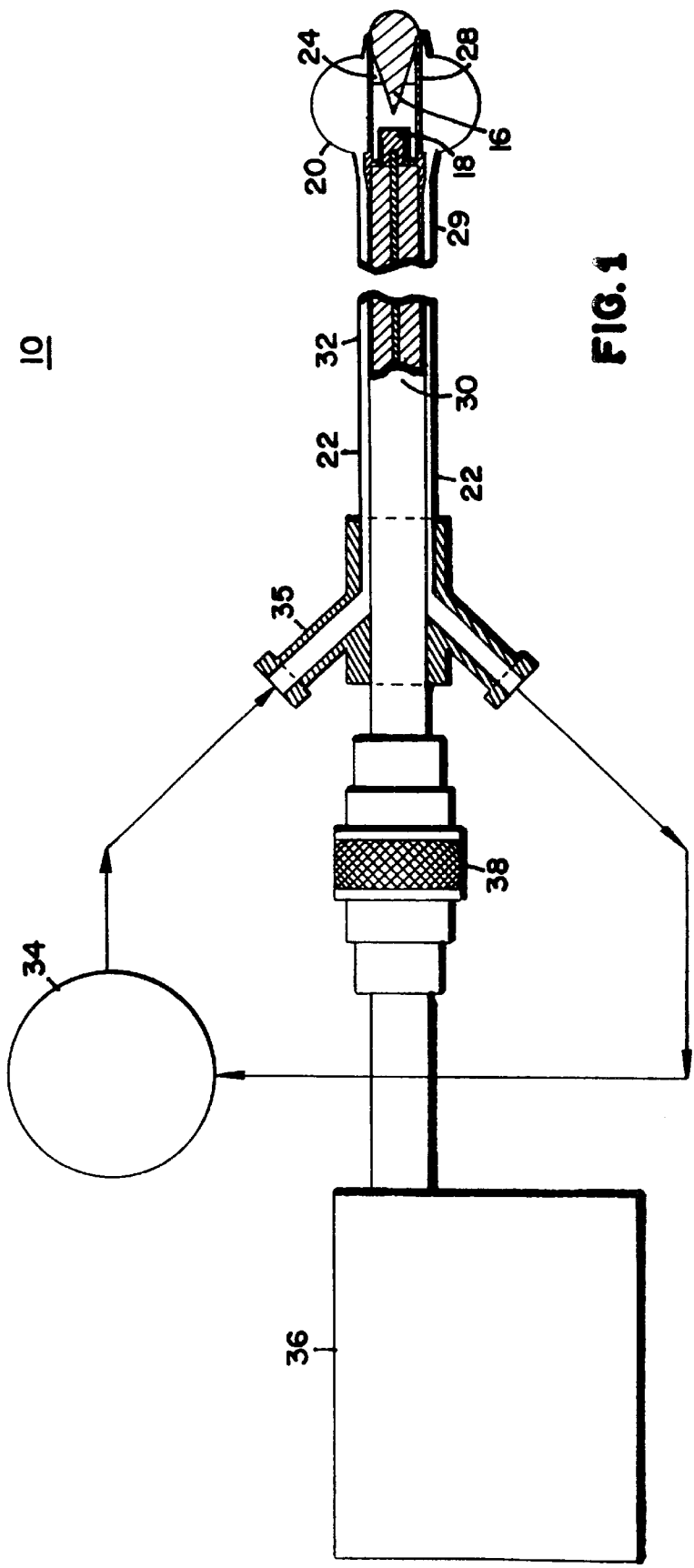
FIG. 1 shows a cross-sectional view of an embodiment of the x-ray device of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

V. DETAILED DESCRIPTION OF THE VARIOUS EMBODIMENTS

The present invention is applicable to a variety of devices, methods of fabrication, methods of use, systems and arrangements which irradiate passages, lumens, vessels, or interior sites in a body with x-ray radiation. An x-ray device of the present invention includes components for producing localized x-ray radiation, that are located within a vacuum housing, and an inflatable balloon surrounding the vacuum housing. The invention is particularly advantageous in treating Barrett's esophagus and pyloric strictures in the gastroesophageal and gastrointestinal systems and other ailments where delivery of localized x-ray radiation to portions of the body not easily accessible is desired. While the present invention is not so limited, an appreciation of various aspects of the invention is best gained through a discussion of application examples operating in such an environment.

Many disease states of the body involve the abnormal thickening of a lumen or passage. The inventors have found that the x-ray device of the present invention provides a very promising way to treat these types of conditions. The x-ray device produces ionizing radiation that penetrates to the first layers of cells on the surface of the passage or lumen. This radiation induces apoptosis, or programmed cell death.

Apoptosis differs from another type of cell death, necrosis. In apoptosis, a disruption in the gene structure of the cell results in the cell failing to replicate, and in some cells, results in an induced cell death where the contents of the cell are utilized by adjacent cells. Cell death by apoptosis therefore reduces inflammation and the biochemical results of inflammation, as compared to necrosis, which results in scarring and thickening of the surface cells.

In one aspect of the present invention, an x-ray device positionable in the esophagus is used to treat Barrett's esophagus by inducing apoptosis in the abnormal cells of the epithelium. The use of the x-ray device of the present invention can therefore be used to reduce the escalation of this condition to cancer. Further, the x-ray device of the present invention can be used for preventing the thickening of the pylorus after dilatation of pyloric strictures.

Now referring to FIG. 1, an embodiment of an x-ray device 10 of the present invention is shown. The x-ray device 10 includes a cathode 16, an anode 18 and a getter 24, all disposed within the vacuum chamber wall 28. These components are shown in FIG. 3 in greater detail.

In the embodiment of FIG. 1, a shaft 29 is shown to permit a physician to maneuver the x-ray device to the treatment site in the body. It is contemplated that different types of maneuvering devices could be employed to position the x-ray device depending on the particular site to be treated, e.g. a passage as illustrated in FIG. 4. In embodiments of the x-ray device used in the esophagus and gastrointestinal systems, the inventors have found that it is helpful for the shaft 29 to be flexible and have a diameter such that it can be easily introduced into the esophagus and pylorus through appropriate flexible endoscopes. In one particular embodiment, the shaft 29 will have an outer diameter of less than or equal to approximately three millimeters, allowing it to fit easily within a standard endoscope, that typically has a working lumen diameter of about three millimeters. In another embodiment, a shaft 29 with an outer diameter of one to two millimeters is used. In other applications, the properties of the shaft may vary to meet the requirements of the task.

For many disorders, an annular or donut-shaped radiation pattern is ideally suited for treatment. In order to achieve this pattern, many passages and other interior portions of the body need to be dilated during the treatment with ionizing radiation from the x-ray device 10. The esophagus is very soft and is in a collapsed state when the patient is not swallowing. One embodiment of the present invention provides a dilating balloon 20 to dilate the passage of the body, such as the esophagus, so that a uniform annular radiation pattern can be created.

The balloon 20 is in fluid communication with a fluid loop 22, that is disposed within the shaft 29 and carries fluid from outside the body to an interior of the balloon 20, and provides a return path for the fluid. The fluid circulates in the interior of the balloon 20, inflating the balloon 20, and is returned to the proximal portion of the shaft 29 through the fluid loop 22. A pump 34 can be used to circulate the fluid and maintain the pressure required to achieve the desired balloon size, and is coupled to the fluid loop 22 via fluid ports 35. Other methods and devices known in the art may also be used to circulate the fluid and inflate the balloon.

When using a small x-ray emitter, a problem is sometimes encountered when too much heat is produced at the anode during operation. In the embodiment of FIG. 1, the fluid circulating through the balloon interior further serves to cool the x-ray emitter and dissipate the potentially damaging heat. Different cooling mechanisms could be also used. When the device is used in a blood vessel, the blood flow through the blood vessel aids in dissipating any heat produced by the unit.

In order to apply an electrical field across the anode and cathode, the anode 18 and the cathode 16 are coupled to a high voltage source 36. In this embodiment, a coaxial cable is disposed within the shaft 29 and coupled to the high voltage source 36 at the proximal end of the shaft 29. An internal conductor 30 of the coaxial cable is coupled to the anode 18 at the appropriate voltage. An external conductive layer 32 of the coaxial cable is held at ground and coupled to the cathode 16. A conductive solder on the outside of the vacuum chamber wall 28 may be used to couple the cathode to the external conductive layer 32. Other known methods may also be used to apply an electric potential across the anode and cathode.

An esophagus in its relaxed state has a diameter of about one to two centimeters, and it cannot accommodate a rigid structure. In one embodiment, the device of the present invention can be disposed within a standard flexible laryngosope or esophagealscope that have a working lumen about 3 millimeters in diameter. Therefore, a coaxial cable used in this device must have a diameter small enough to be accommodated within the passage to be treated or within the scope-device used, and must be able to carry the required voltages and have sufficient flexibility to make turns as it follows the passage. A diameter of less than or equal to three millimeters may be used for most applications, such as in the esophagus. Standard high voltage coaxial cables are generally not flexible enough. The inventors have found that miniature high frequency coaxial cables are available with an outer diameter of approximately 1.0 mm to 3.0 mm which also exhibit sufficient flexibility and can carry the required voltage without breakdown. In one embodiment of the invention, a cable with an outer diameter of less than or equal to about 3 millimeters is used. Cables approximately 1–2 millimeters in diameter are also available, and are used in another embodiment. Such cables are manufactured by, for example, New England Electric Wire Corporation, Lisborn, N.H.

In one embodiment, a getter 24 is disposed within the vacuum housing 28 in order to aid in creating and maintaining a vacuum condition of high quality. The getter 24 has an activation temperature, at which it will react with stray gas molecules in the vacuum. After the vacuum housing is assembled under vacuum conditions and the housing pumped out or baked out, the device is heated to the activation temperature and maintained at that temperature for several hours. It is desirable that the getter used have an activation temperature that is not so high that the x-ray device will be damaged when heated to the activation temperature. A SAES ST 101 alloy getter may be used, which has an activation temperature in the range 750 to 900° C. and is composed of approximately 64% zirconium and 16% aluminum. A ST 707 alloy getter may also be used, which has an activation temperature in the range 300–500° C. and is composed of approximately 70% zirconium, 18.6% vanadium, and 5.4% iron.

Figure 2:
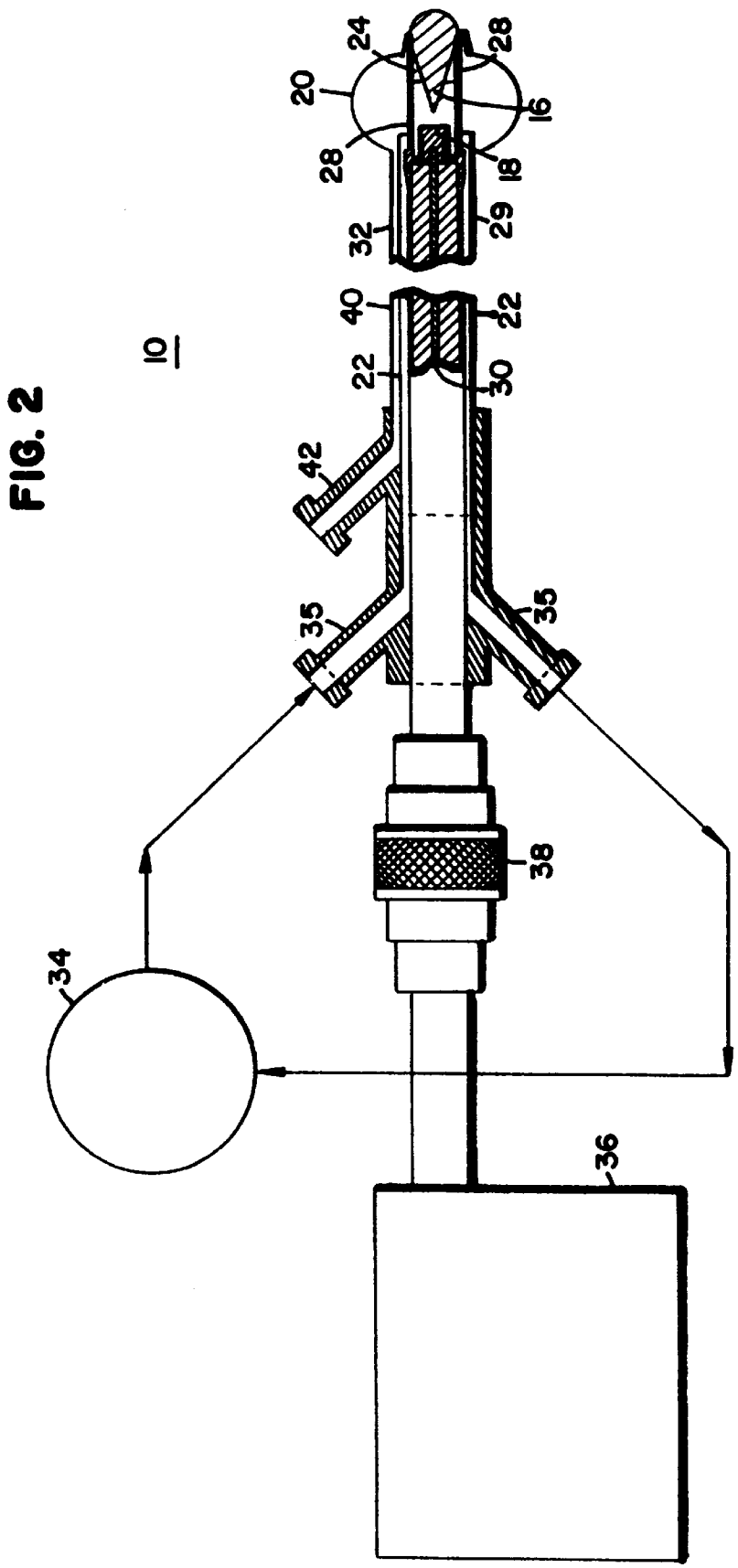
FIG. 2 shows a cross-sectional view of another embodiment of the x-ray device of the present invention.

In order to most effectively decelerate the electrons striking the anode, a heavy metal material can be used for the anode 18, such as tungsten or gold. The cathode and anode will be shaped to produce the desired radiation pattern. In the embodiment of FIGS. 1 and 2, the anode is cylindrically shaped, with a flat, circular side disposed toward the cathode, and the edge is rounded. The cathode of this embodiment is cone shaped.

A wall of the vacuum chamber 28 should be transparent to x-rays in order to allow the full dosage to reach the lumen wall. The wall 28 can comprise pyrolytic boron nitride, or another metal or ceramic material which is transparent to x-rays. Other possibilities include beryllium, beryllium oxide, aluminum, aluminum oxide, or graphite. In one embodiment, the outer diameter of the x-ray device is sized to deliver the localized radiation to the interior of the esophagus. In another embodiment, the outer diameter of the x-ray device is less than or equal to about three millimeters.

In some applications, such as use in the esophagus, the diameter of the dilated balloon should be able to vary with the pressure applied, so that the diameter of the balloon can be adjusted to fit the size of the patient's esophagus or other passage. Therefore, an elastic balloon is particularly suited to the esophageal applications, where the elastic material will conform to the many surface features of the esophagus, and dilate the esophagus more completely. However, in other applications, it may be desirable to employ an inelastic balloon with a fixed dilated diameter.

In the x-ray device, an electric field exists at the cathode 16, while on the outside of the vacuum housing a conductive braid or solder is held at ground. These two potentials can be insulated from each other to reduce the chance of electrical flashover. A vacuum wall of pyrolytic boron nitride can provide some insulation. If a metal is used as the vacuum chamber wall 28, an insulative layer is beneficial to decrease the chance of electrical flashover. As additional protection against electrical flashover, an electrically insulating material can be placed at the joints on the outside of the vacuum chamber wall. The insulating material could be a podding compound, an injection molded polymer, and other materials with electrically insulating properties. The vacuum chamber further includes a biocompatible coating, such as polyethylene, polyurethane or Teflon® material. The joints between the vacuum chamber wall 28 and the anode 18 may be vacuum furnace brazed, or may be sealed by conventional crimping methods.

The cathode of the present invention consists of a material which displays emission characteristics when an electrical field is applied. One possible cathode material is a thin diamond film, which can be formed using conventional chemical vapor deposition techniques. A diamond film may also be formed using a laser ion source as described in U.S. Pat. No. 4,987,007 to Wagal, the contents of which are incorporated herein by reference. A graphite target and the substrate to be coated are disposed in a vacuum chamber. Between the two is an accelerating grid held at a high negative potential. The graphite target is radiated with a focused laser beam from a pulse laser. The laser beam ejects a plume of carbon vapor from the graphite target. A portion of the atoms in the plume are ionized by the focused laser beam, and the positive carbon ions are accelerated towards the substrate by the accelerating grid.

One possible cathode material is described in a U.S. patent application entitled "DEVICE FOR DELIVERING LOCALIZED X-RAY RADIATION TO AN INTERIOR OF A BODY AND METHOD OF MANUFACTURE", having Ser. No. 08/806,244, pending the contents of which are incorporated herein by reference. The cathode material is a coating of carbon having diamond-like bonds which demonstrate negative electron affinity. It is also desirable to have sufficient conductivity to create a constant supply of electrons to the surface of the cathode. The presence of some graphite bonds in the diamond film will contribute to conductivity. Thus a combination of a diamond film having both sp3 carbon bonds, to function as a cathode, and some sp2 carbon bonds, to facilitate conductivity, is particularly suited for use in many applications. Other elements may also be present in the film in small quantities. The diamond film will have the property that it can emit electrons at electrical fields greater than or equal to about 20 KV/micron. This required electric field is significantly lower when compared to that required for metal emitters such as molybdenum or silicon, which require greater than 1,000 KV/micron.

Now referring to FIG. 2, another embodiment of the x-ray device of the present invention is shown. For some types of passages, such as pyloric strictures, the inventors have found that it is desirable to provide independent control of the balloon size and cooling rate. Therefore, a separate inflation lumen 40 and port 42 are provided which are in fluid communication with the balloon 20.

The fluid loop 22 is positioned to circulate cooling fluid to near the anode. In the embodiment shown in FIG. 2, the fluid loop extends to surround a portion of the anode 18. The circulating action of the fluid loop 22 provides a constant cooling rate, regardless of the extent of balloon dilation. The separate inflation lumen 40 can be coupled to a fluid source of adjustable pressure via the inflation port 42. In one embodiment, the fluid loop and inflation lumen are created using plastic extrusion techniques.

When used to radiate the walls of an interior passage, according to one embodiment of the invention, the x-ray device may be placed within a standard endoscope or laryngoscope. The x-ray device is introduced into the passage to be treated. The x-ray device is then guided through the passage, using techniques known in the art, until it is positioned near the area to be radiated. The site to be irradiated may be viewed through the endoscope, and the area around the device may be flushed using the endoscope, if necessary. The dilating balloon is inflated by fluid from the fluid pump to the desired diameter to expand the passage.

The high voltage generator is activated and an electrical field is established across the cathode 16 and the anode 18. The cathode 16 emits electrons which are accelerated toward the anode 18. As the electrons are decelerated by the anode 18, electromagnetic radiation is emitted. In this manner, x-ray radiation is produced by the Bremsstrahlung effect. As the x-ray radiation impinges upon the wall of the passage, such as the pylorus, it inhibits smooth muscle proliferation. Thus, the x-ray device can be used to effectively prevent restenosis. In addition, the x-ray radiation induces cell death of the first layer of the epithelium of the passage by apoptosis, as discussed above. In a Barrett's esophagus, for example, the apoptosis eliminates the layer of abnormal cells and reduces inflammation and the biochemical results of inflammation, thereby preventing scarring and thickening of the surface cells. When the desired dosage has been delivered, the voltage source is discontinued and the balloon is deflated. The device is withdrawn from the body.

The dosage of x-ray radiation to be applied to the interior of a body will generally be within the scope of the attending physicians judgment, and will be based on individual conditions, such as the severity of damage that has occurred at the site to be treated and the particular patient. For example, in order to treat the early stages Barrett's esophagus, only the first layer of cells may need to be irradiated. If Barrett's esophagus has progressed to a cancerous state, the amount of radiation delivered will typically increase.

According to the present invention, x-ray radiation in the range of 10 to 50 Grays may be applied to an area of the interior of the esophagus to treat Barrett's esophagus or prevent restenosis. Preferably, x-ray radiation in the range of 15 to 30 Grays may be applied to an interior body site. The treatment will be structured to last about 2 to 10 minutes, or, more preferably, 3 to 5 minutes. The x-ray emitter may be repositioned during the course of radiation treatment, depending on the length of the area requiring treatment.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention.

What is claimed is:

1. An x-ray device for delivering localized radiation to the interior of a body, comprising:

an anode and a cathode, disposed within a vacuum housing, the anode and the cathode arranged to produce the localized x-ray radiation;

a flexible shaft having distal and proximal portions, where the vacuum housing is coupled to the distal portion of the shaft; and a balloon coupled to and circumferentially surrounding the vacuum housing, the balloon being in fluid communication with a fluid loop for providing a fluid in an interior of the balloon, the balloon being inflatable by the fluid.

2. The device of claim 1, further comprising a getter in the vacuum housing, for improving and maintaining vacuum conditions in the vacuum housing.

3. The device of claim 2, wherein the getter has an activation temperature between about 300 and 900 degrees C.

4. The device of claim 3, wherein the getter comprises material selected from the group consisting of zirconium, aluminum, vanadium, iron, and combinations thereof.

5. The device of claim 1, wherein the shaft further includes a second fluid loop for circulating a fluid to the distal portion of the shaft.

6. The device of claim 1, wherein the shaft and the vacuum housing have an outer diameter less than or equal to 3 millimeters.

7. The device of claim 1, wherein the shaft and the vacuum housing have an outer diameter less than or equal to 2 millimeters.

8. The device of claim 1, wherein the vacuum housing is substantially cylindrical.

9. The device of claim 1, wherein the balloon is elastic.

10. The device of claim 1, wherein the flexible shaft comprises conductors for providing a high voltage.

11. An x-ray device for delivering localized radiation to the interior of a body, comprising:

an anode and a cathode, disposed within a vacuum housing, the anode and the cathode arranged to produce the localized x-ray radiation;

a shaft having distal and proximal portions, where the vacuum housing is coupled to the distal portion of the shaft; and an elastic balloon coupled to and circumferentially surrounding the vacuum housing, the balloon being in fluid communication with a fluid loop for providing a fluid in an interior of the balloon, the balloon being inflatable by the fluid.

12. A method for delivering localized x-ray to an interior passage of a body, comprising:

positioning an x-ray device at the passage to be treated, the x-ray device comprising an x-ray producing unit, a flexible shaft having distal and proximal portions, where a vacuum housing is coupled to the distal portion of the shaft, and a dilating balloon circumferentially surrounding the x-ray producing unit, and a fluid loop for providing a fluid to an interior of the dilating balloon; and applying a high voltage to the x-ray producing unit to produce localized x-ray radiation.

13. The method of claim 12, further comprising inflating the dilation balloon by providing fluid through the fluid loop to the interior of the dilating balloon.

14. The method of claim 12, further comprising cooling the x-ray device with the fluid used to inflate the balloon.

15. The method of claim 12, further comprising providing a cooling fluid loop for circulating cooling fluid to the x-ray device.

* * * * *